United States Patent
Chang et al.

(10) Patent No.: US 8,967,803 B2
(45) Date of Patent: Mar. 3, 2015

(54) IMAGE CAPTURING APPARATUS AND AUTO-FOCUSING METHOD THEREOF

(75) Inventors: Tso-Yu Chang, New Taipei (TW); Yu-Fen Chung, Hsinchu (TW); Te-Chao Tsao, Hsinchu County (TW); Pin-Wen Chen, Changhua County (TW); Shin-Hao Cheng, Taichung (TW); Peng-Hsiang Wang, Hsinchu (TW); Ching-Chung Hsu, Kaohsiung (TW); Chun-An Lin, Hsinchu (TW)

(73) Assignee: Altek Corporation, Hsinchu (TW)

( * ) Notice: Subject to any disclaimer, the term of this patent is extended or adjusted under 35 U.S.C. 154(b) by 244 days.

(21) Appl. No.: 13/606,031

(22) Filed: Sep. 7, 2012

(65) Prior Publication Data

US 2014/0016092 A1 Jan. 16, 2014

(30) Foreign Application Priority Data

Jul. 12, 2012 (TW) .............................. 101125132 A

(51) Int. Cl.
*A61B 3/14* (2006.01)
(52) U.S. Cl.
USPC ...................................................... 351/206
(58) Field of Classification Search
USPC .................. 351/205, 206, 210, 212, 246, 216
See application file for complete search history.

(56) References Cited

U.S. PATENT DOCUMENTS

2008/0278687 A1* 11/2008 Somani .......................... 351/208
2012/0287255 A1* 11/2012 Ignatovich et al. ............. 348/78

* cited by examiner

Primary Examiner — Scott J Sugarman
Assistant Examiner — Mustak Choudhury
(74) Attorney, Agent, or Firm — Jianq Chyun IP Office

(57) ABSTRACT

An image capturing apparatus and an auto-focusing method thereof are provided. The method includes transmitting light beams from light sources to an eye including a cornea, a pupil, a crystalline lens, and a fundus. The light beams are transmitted to the cornea through the cornea. The light beams transmitted to the cornea form first light point images detected by an image sensor through a lens module having first and second lenses. According to the first light point images and focal adjustment data, the first lens and the light sources are moved simultaneously to focus on the cornea. The light beams are substantially intersected at the pupil and transmitted to the fundus to form second light point images detected by the image sensor through the lens module. According to the second light point images and the focal adjustment data, the first lens is moved to focus on the fundus.

13 Claims, 7 Drawing Sheets

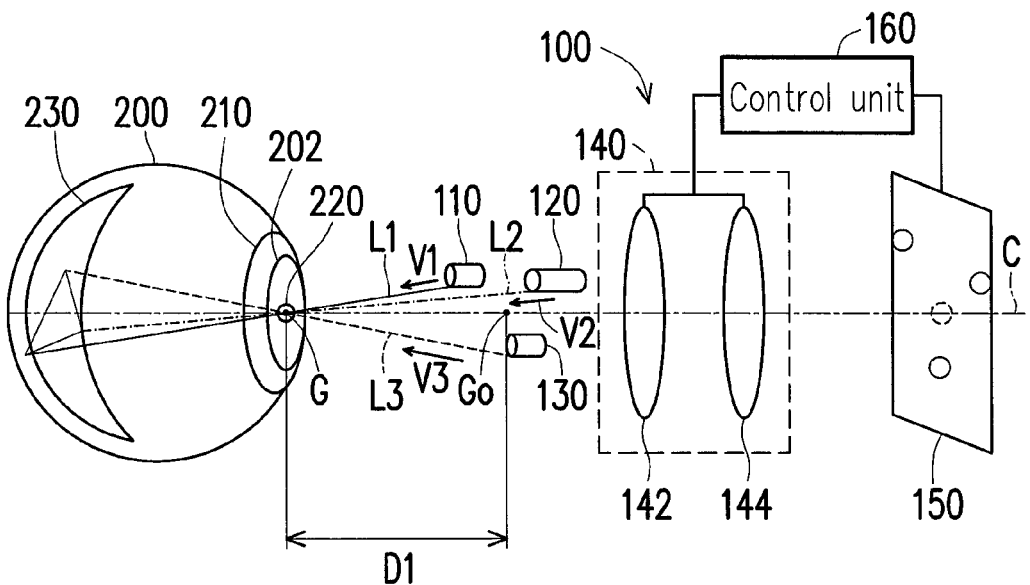

FIG. 1

| Transmitting light beams from light sources to an eye, wherein the eye has a cornea, a pupil, and a fundus, and the light beams are transmitted to the fundus through the cornea | ~S201 |

| Detecting first light point images on the cornea by an image sensor through a lens module, wherein the lens module has a first lens and a second lens | ~S203 |

| Simultaneously moving the first lens according to the first light point images and focal adjustment data, so as to focus on the cornea | ~S205 |

| Detecting second light point images on the fundus by the image sensor through the lens module, wherein the second light point images are generated by substantially intersecting light beams at the pupil and transmitting the light beams to the fundus | ~S207 |

| Moving the first lens according to the focal adjustment data as well as the second light point images, so as to focus on the fundus | ~S209 |

FIG. 2

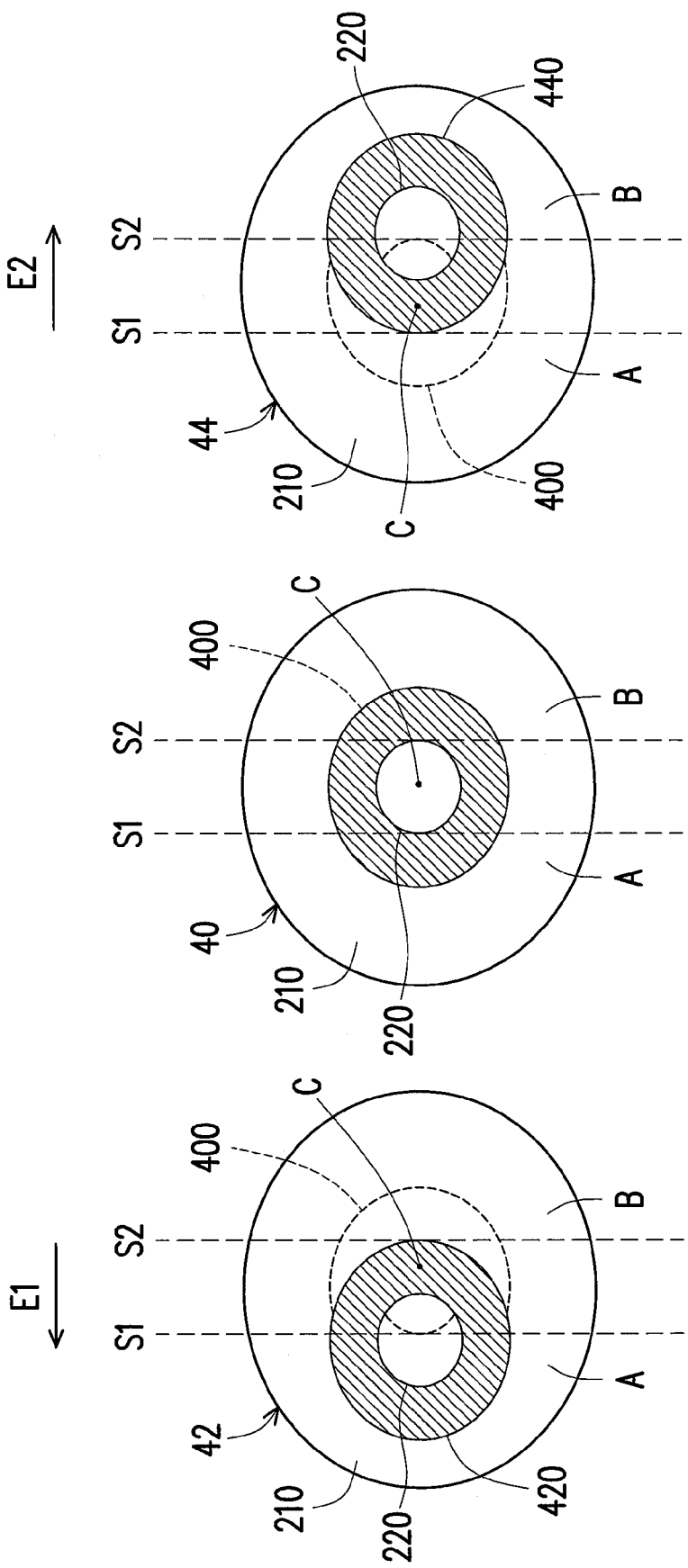

IMAGE CAPTURING APPARATUS AND AUTO-FOCUSING METHOD THEREOF

CROSS-REFERENCE TO RELATED APPLICATION

This application claims the priority benefit of Taiwan application serial no. 101125132, filed on Jul. 12, 2012. The entirety of the above-mentioned patent application is hereby incorporated by reference herein and made a part of this specification.

BACKGROUND OF THE INVENTION

1. Field of Invention

The invention relates to an image capturing apparatus and an auto-focusing method of the image capturing apparatus. More particularly, the invention relates to an image capturing apparatus applied for fundus examination and an auto-focusing method of the image capturing apparatus.

2. Background

The saying goes that human eyes are the window to the soul, and thus eye health is vital to human beings. The blood vessels may be directly seen from observing the fundus of an eye, such that the fundus examination may be performed periodically to track and inspect systematic disease, especially blood vessel lesions (e.g., diabetic retinopathy). Common ocular inspection apparatuses include pneumatonometers, refracting instruments, fundus cameras, and so on. Here, the fundus camera is an image capturing apparatus for capturing an image of the fundus of an eye, so as to facilitate diagnosis of ocular lesions.

A conventional image capturing apparatus for fundus examination is required to be able to adjust an imaging focal distance to the fundus of an eye in compliance with curvatures of different eye surfaces to be tested, and thereby the clear fundus image can be captured. For instance, according to the related art, light beams generated by two rectangular illuminating slits are refracted to an image sensor to be detected. The light beams enter a crystalline lens of an eye in parallel, and the light beams are refracted and focused on locations around the retina of the fundus. After the locations of two light points obtained by refracting the light beams back to the image sensor are calculated, the location of the focal point may be acquired for moving the lens and focusing on the retina of the fundus.

However, according to the related art, the image sensor need be aligned to the pupil manually, and the image sensor can focus on the fundus of an eye after the pupil is already aligned to the image sensor. The manual alignment of the image sensor to the pupil during the fundus examination is inconvenient and consumes significant time.

SUMMARY OF THE INVENTION

The invention is directed to an auto-focusing method of an image capturing apparatus. The auto-focusing method allows an image capturing apparatus to focus on a cornea and simultaneously obtain a distance from a fundus to the cornea, so as to reduce the time spent on focusing on the fundus.

The invention is further directed to an image capturing apparatus that is able to focus on the cornea and simultaneously obtain the distance from the fundus to the cornea, so as to reduce the time spent on focusing on the fundus.

In an embodiment of the invention, an auto-focusing method of an image capturing apparatus is provided. The auto-focusing method includes following steps. A plurality of light beams is transmitted from a plurality of light sources to an eye. The eye includes a cornea, a pupil, a crystalline lens, and a fundus. The light beams are transmitted to the fundus through the cornea. A plurality of first light point images on the cornea are detected by an image sensor through a lens module. Here, the first light point images are generated by transmitting the light beams to the cornea, and the lens module has a first lens and a second lens. According to the first light point images and focal adjustment data, the light sources and the first lens are moved simultaneously to focus on the cornea. A plurality of second light point images on the fundus are detected by the image sensor through the lens module. Here, the second light point images are generated by substantially intersecting the light beams at the pupil and transmitting the light beams to the fundus. According to the second light point images and the focal adjustment data, the first lens of the lens module is moved to focus on the fundus.

According to an embodiment of the invention, the step of moving the first lens of the lens module according to the first light point images and the focal adjustment data to focus on the cornea includes calculating a first set of location data of the first light point images. A first displacement corresponding to the first set of location data is obtained from the focal adjustment data according to the first set of location data. The first lens and the light sources are adjusted according to the first displacement.

According to an embodiment of the invention, the auto-focusing method of the image capturing apparatus further includes following steps. A cornea image of the cornea is detected, and a reflection difference of the cornea image is obtained according to distribution of the cornea image. The first lens is adjusted according to the reflection difference and correction data, and the reflection difference is obtained every other time sequence according to the distribution of the cornea image.

According to an embodiment of the invention, the step of detecting the second light point images on the fundus by the image sensor through the lens module includes obtaining a distance from the cornea to the fundus according to the second light point images and the focal adjustment data.

According to an embodiment of the invention, the step of detecting the second light point images on the fundus by the image sensor through the lens module further includes calculating a second set of location data of the second light point images. A second displacement corresponding to the second set of location data is obtained from the focal adjustment data according to the second set of location data. The first lens is adjusted according to the second displacement.

According to an embodiment of the invention, the auto-focusing method further includes detecting the first light point images by the image sensor through the first lens and detecting the second light point images by the image sensor through the first lens.

In an embodiment of the invention, an image capturing apparatus that includes a plurality of light sources, an image sensor, a lens module, and a control unit is provided. The light sources transmit a plurality of light beams to an eye. Here, the eye includes a cornea, a pupil, a crystalline lens, and a fundus, and the light beams are transmitted to the fundus through the cornea. The lens module is disposed between the light sources and the image sensor and has a first lens and a second lens. The control unit is coupled to the image sensor and the lens module. The image sensor detects a plurality of first light point images on the cornea through a lens module, and the first light point images are generated by transmitting the light beams to the cornea. The control unit simultaneously moves the light sources and the first lens according to the first light point images and focal adjustment data, such that the image sensor focuses on the cornea. The image sensor detects a plurality of second light point images on the fundus through the lens module, and the second light point images are generated by substantially intersecting the light beams at the pupil and transmitting the light beams to the fundus. The control unit moves the first lens of the lens module according to the second light point images and the focal adjustment data, such that the image sensor focuses on the fundus.

According to an embodiment of the invention, the control unit calculates a first set of location data of the first light point images, obtains a first displacement corresponding to the first set of location data from the focal adjustment data according to the first set of location data, and adjusts the first lens and the light sources according to the first displacement.

According to an embodiment of the invention, the image sensor detects a cornea image of the cornea, and the control unit obtains a reflection difference of the cornea image according to distribution of the cornea image and adjusts the first lens according to the reflection difference and correction data.

According to an embodiment of the invention, the image capturing apparatus further includes a time sequence control unit coupled to the control unit, and the time sequence control unit informs the control unit every other time sequence to obtain the reflection difference of the cornea image according to the distribution of the cornea image.

According to an embodiment of the invention, the control unit obtains a distance from the cornea to the fundus according to the second light point images and the focal adjustment data.

According to an embodiment of the invention, the control unit calculates a second set of location data of the second light point images, obtains a second displacement corresponding to the second set of location data from the focal adjustment data according to the second set of location data, and adjusts the first lens according to the second displacement.

According to an embodiment of the invention, the image sensor detects the first light point images and the second light point images through the first lens.

In view of the above, the image capturing apparatus may focus on the cornea by detecting the first light point images that are obtained by transmitting the light beams to the cornea and may then focus on the fundus by detecting the second light point images transmitted to the fundus. Thereby, when the image capturing apparatus completely focuses on the cornea, the image capturing apparatus may also obtain the distance from the fundus to the cornea through moving the lens to acquire the location data of the second light point images, and the image capturing apparatus then completely focuses on the fundus. As a result, by applying the image capturing apparatus described herein, the time spent on focusing on the fundus may be reduced.

Several exemplary embodiments accompanied with figures are described in detail below to further explain the invention.

BRIEF DESCRIPTION OF THE DRAWINGS

The accompanying drawings are included to provide further understanding, and are incorporated in and constitute a part of this specification. The drawings illustrate exemplary embodiments and, together with the description, serve to explain the principles of the disclosure.

FIG. 1 is a block diagram illustrating an image capturing apparatus according to an embodiment of the invention.

FIG. 2 is a flow chart illustrating an auto-focusing method of an image capturing apparatus according to an embodiment of the invention.

FIG. 4A to FIG. 4C are schematic views illustrating tracking of a cornea image according to an embodiment of the invention.

DETAILED DESCRIPTION OF DISCLOSED EXEMPLARY EMBODIMENTS

Figure 3A:
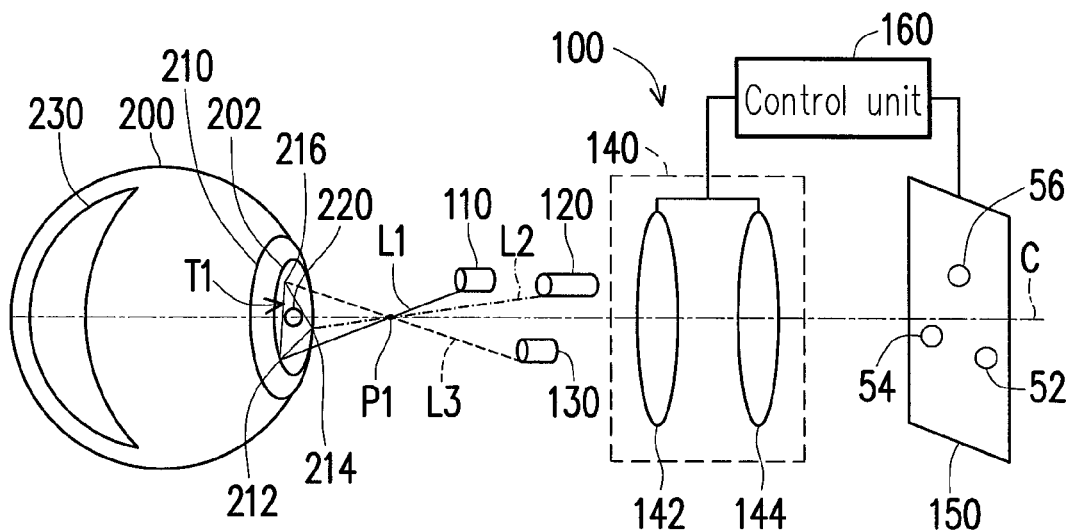
FIG. 3A, FIG. 3C, and FIG. 3E are block diagrams illustrating an image capturing apparatus that detects first light point images according to an embodiment of the invention.

During fundus examination, if the apparatus used for the examination may rapidly focus on the cornea and the fundus of an eye in response to various curvatures of different eye surfaces and may further capture clear images on the fundus, the efficiency of fundus examination may be ameliorated. Accordingly, the invention is directed to an image capturing apparatus and an auto-focusing method of the image capturing apparatus. In order to make the invention more comprehensible, embodiments are described below as examples to demonstrate that the invention can actually be implemented.

FIG. 1 is a block diagram illustrating an image capturing apparatus according to an embodiment of the invention. The image capturing apparatus 100 described in the present embodiment is a fundus camera or any other optometry instruments. With reference to FIG. 1, the image capturing apparatus 100 includes a plurality of light sources 110, 120, and 130, a lens module 140, an image sensor 150, and a control unit 160. According to the present embodiment, the image capturing apparatus 100 serves to detect an eye 200 that has a cornea 210, a pupil 220, a crystalline lens 202, and a fundus 230. The fundus 230 has a retina, optic nerves, a choroid, and other tissues (not shown).

Specifically, the light sources 110, 120, and 130 emit a plurality of light beams L1, L2, and L3 that are transmitted to the fundus 230 through the cornea 210. In the present embodiment, the light sources 110, 120, and 130 are invisible light sources (e.g., far infrared light sources), and the light beams L1, L2, and L3 are invisible light beams (e.g., far infrared light beams). Besides, the light sources 110, 120, and 130 described in the present embodiment may provide the light beams characterized by favorable rectilinearity. Particularly, the light beam L1 is substantially transmitted along a direction V1, the light beam L2 is substantially transmitted along a direction V2, and the light beam L3 is substantially transmitted along a direction V3. The directions V1, V2, and V3 are not parallel to one another. In the present embodiment, each light source 110, 120, and 130 may respectively emit the light beams L1, L2, and L3 at fixed projection angles, such that the light beams L1, L2, and L3 are intersected at an intersection point G, and a focusing distance D1 from a center location Go of each light source 110, 120, and 130 to the intersection point G may be determined. In other embodiments, the projection angles at which the light sources 110, 120, and 130 emit the light beams L1, L2, and L3 may be adjusted according to the images captured by the image capturing apparatus 100, and thereby the location of the intersection point G of the light beams L1, L2, and L3 may be controlled. To better illustrate the invention, only three light sources are shown in FIG. 1. However, the number of the light sources is not limited in the present embodiment. A person having ordinary skill in the art may change the number of the light sources in the image capturing apparatus 100 based on actual design demands with reference to the teachings of the present embodiment.

The lens module 140 is configured between the image sensor 150 and the light sources 110, 120, and 130. Here, the lens module 140 has a first lens 142 and a second lens 144, and the second lens 144 represents a combination of basic lenses. In the present embodiment, the first lens 142 of the lens module 140 may be coupled to or separated from the fixing base (not shown) of each light source 110, 120, and 130, such that the first lens 142 may be moved together or not together with the light sources 110, 120, and 130. In particular, when the light sources 110, 120, and 130 emit the light beams L1, L2, and L3 at the fixed angles, the first lens 142 may be moved back and forth on a light axis C together with the light sources 110, 120, and 130, such that the intersection point G of the light beams L1, L2, and L3 is located at the pupil 220 of the eye 200. Thereby, the image sensor 150 may focus on the cornea 210, and a cornea image may be clearly displayed on the image sensor 150. After the image sensor 150 completely focuses on the cornea 210, the arrangement of the first lens 142 will no longer be subject to the light sources 110, 120, and 130. Namely, the first lens 142 is separated from the fixing base of each light source 110, 120, and 130, and the first lens 142 may be moved back and forth or rotated on the light axis C, such that the image sensor 150 may further focus on the fundus 230. The collaborative configurations of the first lens 142, the second lens 144, and the light sources 110, 120, and 130 allow the image capturing apparatus 100 to focus on the fundus 230 in an expedited manner, and the clarity of the captured fundus image may be enhanced.

The sensing region of the image sensor 150 may have an imaging surface (not shown). The cornea image on the cornea 210 and the fundus image on the fundus 230 may be imaged on the imaging surface of the image sensor 150 through the lens module 140. The image sensor 150 described in the present embodiment is, for instance, a charge coupled device (CCD), a complementary metal-oxide semiconductor (CMOS) device, a photo-sensing film, and so on.

The control unit 160 is coupled to the image sensor 150, the first lens 142, and the second lens 144. In the present embodiment, the control unit 160 controls the arrangement of the first lens 142 and the light sources 110, 120, and 130 on the light axis C according to the image of the eye 200 detected by the image sensor 150 and focal adjustment data, such that the image sensor 150 focuses on the cornea 210. Besides, the control unit 160 controls the arrangement of the first lens 142 on the light axis C, such that the image sensor 150 focuses on the fundus 230.

The auto-focusing method of the image capturing apparatus is described below in view of the aforesaid image capturing apparatus 100 and the eye 200. FIG. 2 is a flow chart illustrating an auto-focusing method of an image capturing apparatus according to an embodiment of the invention. The auto-focusing method described in the present embodiment is suitable for detecting the eye 200 through the image capturing apparatus 100.

With reference to FIG. 1 and FIG. 2, in step S201, the light sources 110, 120, and 130 emit the light beams L1, L2, and L3 to the eye 200. Here, the light beams L1, L2, and L3 are transmitted to the fundus 230 through the cornea 210 of the eye 200. In the present embodiment, the light sources 110, 120, and 130 may be arranged in a triangular manner and may emit the light beams L1, L2, and L3 that are not parallel to one another.

In step S203, the image sensor 150 detects a plurality of first light point images on the cornea 210 through the lens module 140. Here, the first light point images are generated by transmitting the light beams L1, L2, and L3 to the cornea 210. The image sensor 150 may also detect the first light point images directly through the first lens 142 and the second lens 144 of the lens module 140.

Figure 3B:
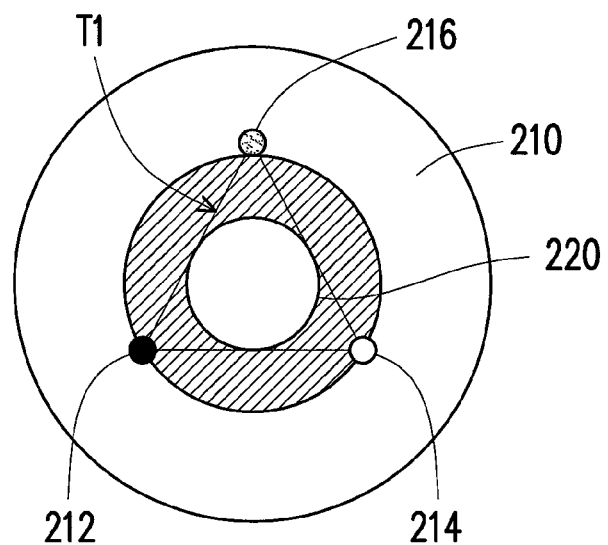
FIG. 3B is a schematic diagram illustrating distribution of the first light point images correspondingly depicted in FIG. 3A.
Figure 3C:
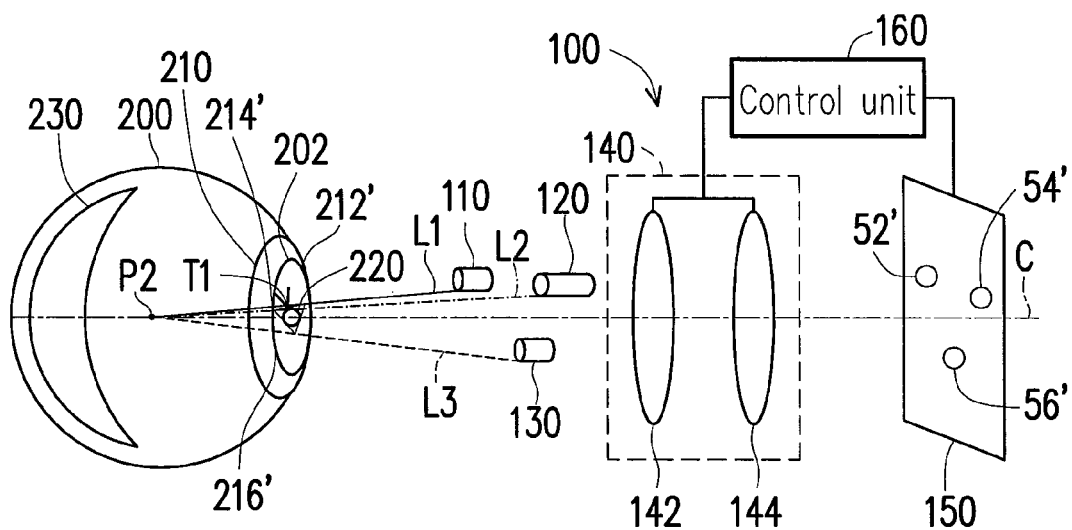
Figure 3D:
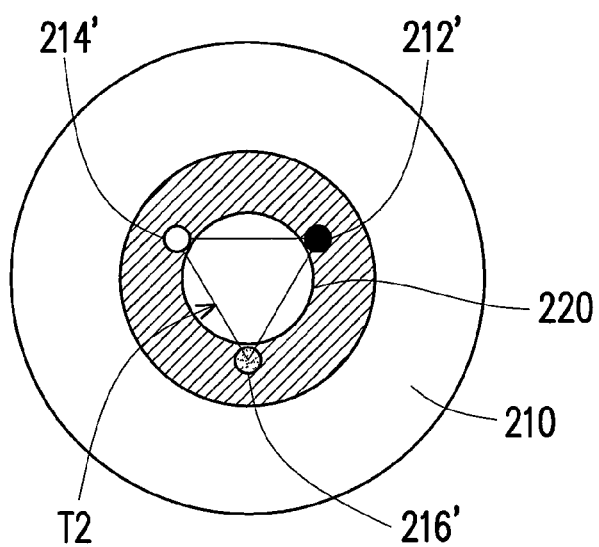
FIG. 3D is a schematic diagram illustrating distribution of the first light point images correspondingly depicted in FIG. 3C.
Figure 3E:
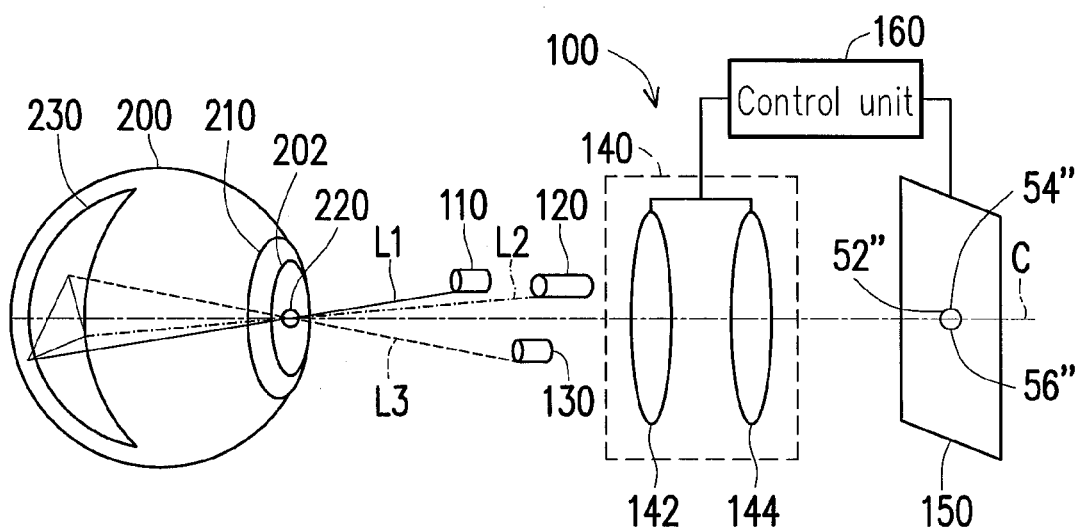
Figure 3F:
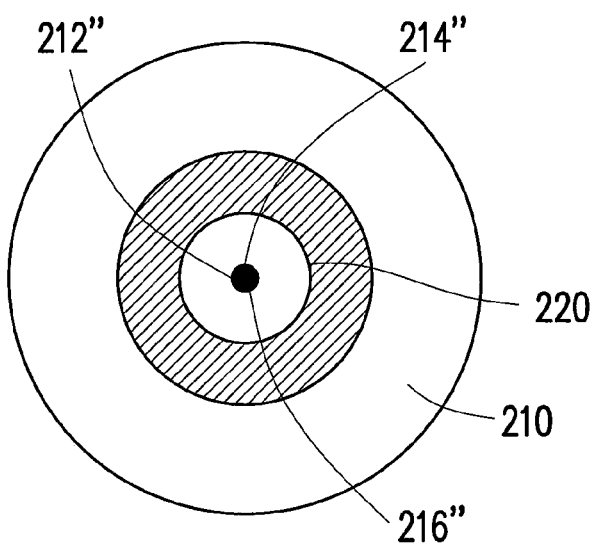
FIG. 3F is a schematic diagram illustrating distribution of the first light point images correspondingly depicted in FIG. 3E.

Particularly, FIG. 3A, FIG. 3C, and FIG. 3E are block diagrams illustrating an image capturing apparatus that detects first light point images according to an embodiment of the invention. FIG. 3B is a schematic diagram illustrating distribution of the first light point images correspondingly depicted in FIG. 3A. FIG. 3D is a schematic diagram illustrating distribution of the first light point images correspondingly depicted in FIG. 3C. FIG. 3F is a schematic diagram illustrating distribution of the first light point images correspondingly depicted in FIG. 3E. It is assumed herein that the non-parallel light beams L1, L2, and L3 emitted from the light sources 110, 120, and 130 are distributed in a regular-triangular manner and transmitted toward the eye 200 before the light beams L1, L2, and L3 are intersected. With reference to FIG. 3A and FIG. 3B, when the light beams L1, L2, and L3 detected by the image sensor 150 through the lens module 140 are intersected at a intersection point P1 between the cornea 210 and the light sources 110, 120, and 140 (i.e., in front of the cornea 210), the distribution of the first light point images 212, 214, and 216 which are transmitted to the cornea 210 and detected by the image sensor 150 is shaped as a regular triangle T1, and the images 52, 54, and 56 located on the imaging surface of the image sensor 150 respectively correspond to the first light point images 212, 214, and 216. With reference to FIG. 3C and FIG. 3D, when the light beams L1, L2, and L3 detected by the image sensor 150 through the lens module 140 are intersected at a intersection point P2 between the cornea 210 and the fundus 230 (i.e., on back of the cornea 210), the distribution of the first light point images 210', 212', and 214' which are transmitted to the cornea 210 and detected by the image sensor 150 is shaped as an inverted triangle T2, and the images 52', 54', and 56' located on the imaging surface of the image sensor 150 respectively correspond to the first light point images 212', 214', and 216'. Note that each first light point image described above has a nearly circular shape, and the area and the shape of the first light point images are not limited in the present embodiment.

With reference to FIG. 1 and FIG. 2, in step S205, the control unit 160 moves the first lens 142 according to the first light point images and focal adjustment data, so as to focus on the cornea 210. In particular, to allow the light beams L1, L2, and L3 to be intersected at the cornea 210 and enter the eye 200, the control unit 160 calculates a first set of location data of the first light point images. According to the first set of location data, the control unit 160 may obtain a first displacement corresponding to the first set of location data from the focal adjustment data. Here, the focal adjustment data are, for instance, stored in a storage apparatus (not shown) coupled to the control unit 160. To be specific, the first light point images detected by the image sensor 150 through the lens module 140 may be distributed in a different manner by simultaneously adjusting the light sources 110, 120 and 130 and the first lens 142, and therefore the focal adjustment data may include parameters required by the image sensor 150 for focusing on the cornea 210. For instance, the focal adjustment data includes a plurality of differences between the predetermined location data O1 and different first sets of location data as well as the first displacements of the first lens 142 (i.e., the moving distance of the first lens 142 on the light axis C) corresponding to the differences. That is, when the light sources 110, 120, and 130 respectively emit the light beams L1, L2, and L3 at the fixed angles, the control unit 160 adjusts the first lens 142 according to the first displacement. At the same time, the light sources 110, 120, and 130 and the first lens 142 are simultaneously moved on the light axis C, and the light beams L1, L2, and L3 are then intersected at the pupil 220 and transmitted to the fundus 230, such that the image sensor 150 may focus on the cornea 210. Certainly, in other embodiments, when the projection angles at which the light sources 110, 120, and 130 respectively emit the light beams L1, L2, and L3 are adjustable, the control unit 160 may also adjust the projection angle of each light source 110, 120, and 130 according to the first displacement, and the light beams L1, L2, and L3 are then intersected at the pupil 220 and transmitted to the fundus 230. Thereby, the image sensor 150 may still focus on the cornea 210.

In particular, as illustrated in FIG. 3A and FIG. 3B, the distribution of the first light point images 212, 214, and 216 detected by the image sensor 150 is shaped as a regular triangle T1. Here, the control unit 160 calculates a first set of location data R1 of the first light point images 212, 214, and 216, and the control unit 160 may, based on the first set of location data R1, calculate distance and vector difference among the first light point images 212, 214, and 216. In addition, the control unit 160 obtains a first displacement X1 corresponding to the first set of location data R1 from the focal adjustment data and adjusts the first lens 142 according to the first displacement X1. As shown in FIG. 3E and FIG. 3F, the image sensor 150 detects the first light point images 212", 214", and 216" that are intersected at the pupil 220, i.e., the first light point images 212", 214", and 216" are overlapped. Here, the light beams L1, L2, and L3 are intersected at the pupil 220 and enter the eye 200, and the images 52", 54", and 56" located on an imaging surface of the image sensor 150 respectively correspond to the first light point images 212", 214", and 216".

From another perspective, as illustrated in FIG. 3C and FIG. 3D, the distribution of the first light point images 212', 214', and 216' detected by the image sensor 150 is shaped as an inverted triangle T2. Likewise, the control unit 160 calculates a first set of location data R1' of the first light point images 212', 214', and 216', and the control unit 160 may, based on the first set of location data R1', calculate distance and vector difference among the first light point images 212', 214', and 216'. In addition, the control unit 160 obtains a first displacement X1' corresponding to the first set of location data R1' from the focal adjustment data and adjusts the first lens 142 according to the first displacement X1'. At this time, as illustrated in FIG. 3E and FIG. 3F, the image sensor 150 detects the first light point images 212", 214", and 216" that are intersected at the pupil 220 and overlapped with one another.

During the detection of the eye 200 by the image sensor 150, the relative position of the eye 200 and the light axis C does not necessarily remain unchanged; therefore, in order for the image sensor 150 to keep the light beams L1, L2, and L3 to be intersected at the pupil 220, the control unit 160 may obtain a reflection difference of a cornea image according to distribution of the cornea image. Besides, the control unit 160 may adjust the first lens according to the reflection difference and correction data. Here, the correction data may include parameters respectively corresponding to various reflection differences; thereby, the control unit 160 may adjust the first lens 142 to track the cornea image, the light beams L1, L2, and L3 detected by the image sensor 150 may be intersected at the pupil 220, and thus the image sensor 150 may consistently focus on the cornea 210.

FIG. 4A to FIG. 4C are schematic views illustrating tracking of a cornea image according to an embodiment of the invention. Here, FIG. 4A shows an image captured by the image sensor 150 when the pupil 220 is shifted toward a first direction E1; FIG. 4B shows an image captured by the image sensor 150 when the pupil 220 remains not shifted; FIG. 4C shows an image captured by the image sensor 150 when the pupil 220 is shifted toward a second direction E2. For the purpose of clear illustration, in FIG. 4A to FIG. 4C, the cornea image captured by the image sensor 150 is divided into regions A and B by dotted lines S1 and S2, and the region A and the region B are respectively located at two sides of the dotted lines S1 and S2.

Specifically, after the image sensor 150 focuses on the cornea 210, as illustrated in FIG. 4B, the reflection of the cornea image 40 at the regions A and B is equal (e.g., the circular area 400 is equally distributed in the regions A and B). When the cornea 210 and the light axis C of the image sensor 150 are relatively moved, and the pupil 220 detected by the image sensor 150 is shifted toward the first direction E1, the reflection of the cornea image 42 (i.e., the circular area 420) is mainly located in the region A, as shown in FIG. 4A. Hence, the control unit 160 obtains a reflection difference by calculating the difference in reflection at the regions A and B. The control unit 160 may further compare the reflection difference with correction data, so as to adjust the first lens 142 and further equalize the reflection at the regions A and B. When the eye 200 and the light axis C of the image sensor 150 are relatively moved, and the pupil 220 detected by the image sensor 150 is shifted toward the second direction E2, the reflection of the cornea image 44 (i.e., the circular area 440) is mainly located in the region B, as shown in FIG. 4C. Similarly, the control unit 160 may obtain a reflection difference by calculating the difference in reflection at the regions A and B and compare the reflection difference with the correction data, so as to adjust the first lens 142 and further equalize the reflection at the regions A and B. As such, in case of external disturbance, the control unit 160 may timely adjust the first lens 142 by tracking the reflection difference of the cornea image. Thereby, the image sensor 150 may keep the light axis of the first lens 142 to be located at the center position of the pupil 220.

The control unit 160 may be coupled to a time sequence control unit (not shown), and the time sequence control unit informs the control unit 160 every other time sequence to obtain the difference in reflection at the regions A and B, so as to obtain the reflection difference of the cornea image. Thereby, the control unit 160 may, according to the time sequence, examine whether the light beams L1, L2, and L3 are constantly intersected at the pupil 220 and transmitted to the fundus 230, such that the image sensor 150 may consistently focus on the cornea 210.

In step S207, the image sensor 150 detects a plurality of second light point images on the fundus 230 through the lens module 140. Here, the second light point images are generated by substantially intersecting the light beams L1, L2, and L3 at the pupil 220 and transmitting the light beams L1, L2, and L3 to the fundus 230. Specifically, as shown in FIG. 5A to FIG. 5C, the distances from the pupils 220 to the fundus 230 in different eyes 210 are different, and therefore the distribution of the second light point images detected by the image sensor 150 through the lens module 140 is different.

In step S209, the control unit 160 moves the first lens 142 according to the focal adjustment data as well as the second light point images detected by the image sensor 150, so that the image sensor 150 can focus on the fundus 230. In particular, the control unit 160 calculates a second set of location data of the second light point images, e.g., distance and vector difference among the second light point images. Besides, the control unit 160 may obtain a second displacement corresponding to the second set of location data from the focal adjustment data. Here, the focal adjustment data may include parameters required by the image sensor 150 for focusing on the fundus 230, such that the control unit 160 may calculate the distance from the fundus 230 to the cornea 210 and thereby control the image sensor 150 to focus on the fundus 230. For instance, the focal adjustment data include a plurality of differences between the predetermined location data O2 and different second sets of location data as well as the second displacements of the first lens 142 (i.e., the moving distance of the first lens 142 on the light axis C or the angle at which the first lens 142 rotates on the light axis C) corresponding to the differences. Therefore, the control unit 160 allows the image sensor 150 to detect clear fundus images after the control unit 160 adjusts the first lens 142 according to the second displacement.

Figure 5A:
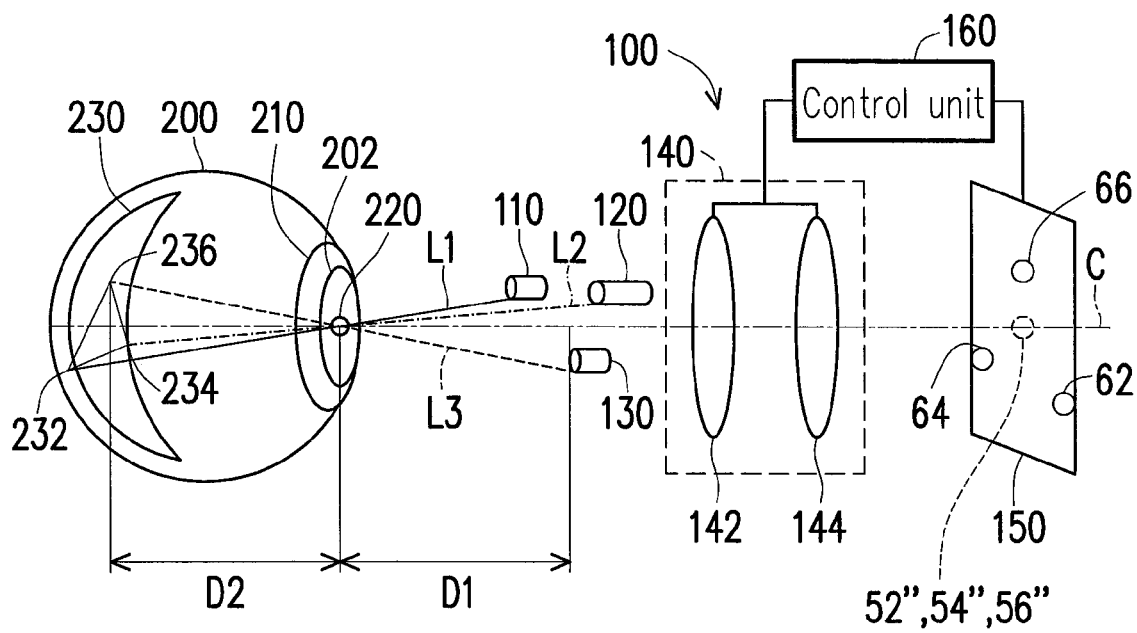
FIG. 5A to FIG. 5C are schematic views illustrating detection of a fundus image according to an embodiment of the invention.
Figure 5B:
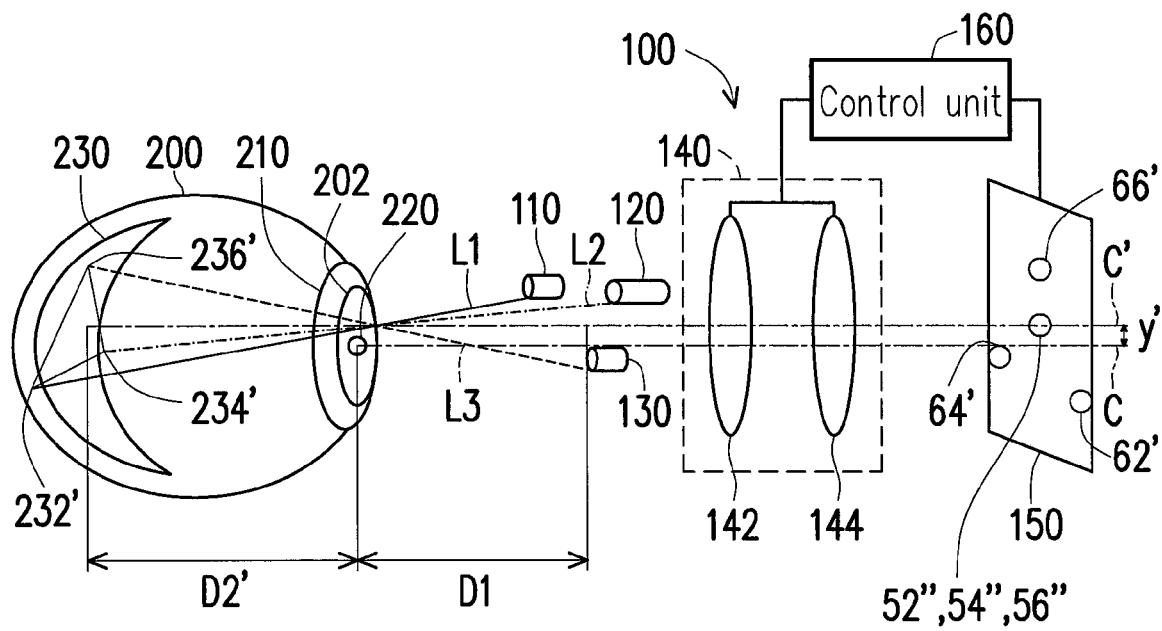
Figure 5C:
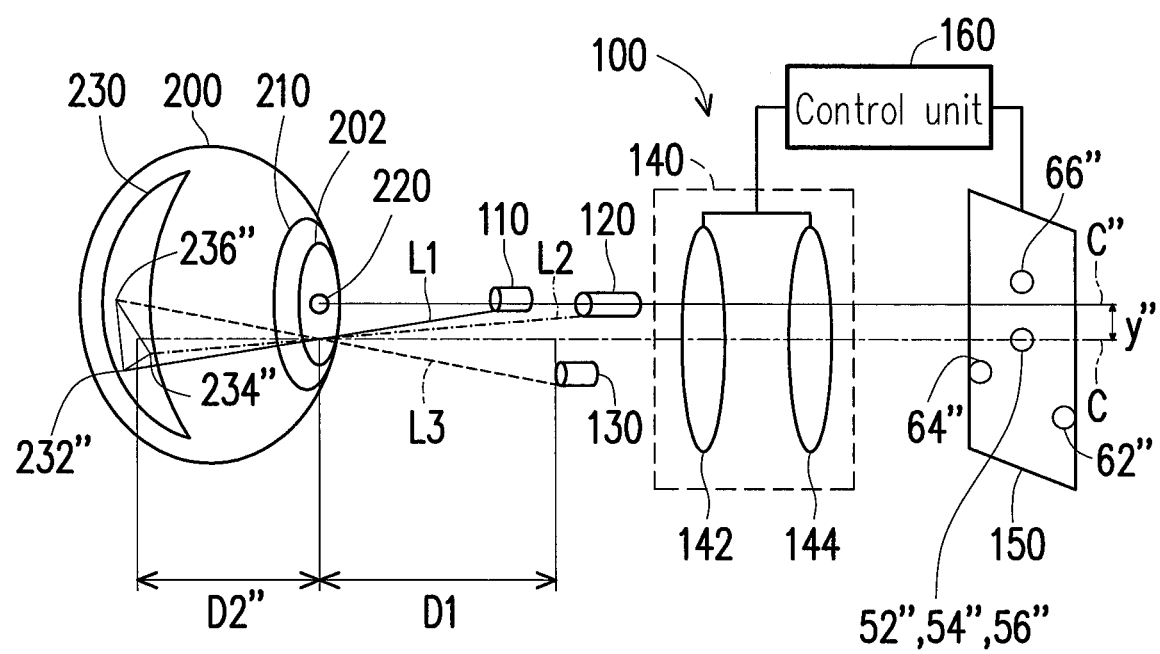

In particular, as shown in FIG. 5A, the image sensor 150, after focusing on the cornea 210, simultaneously detects the second light point images 232, 234, and 236 on the fundus 230. At this time, the control unit 160 may obtain the distance D2 from the cornea 210 to the fundus 230 according to the second set of location data R2 of the second light point images 232, 234, and 236 and obtain the second displacement X2 corresponding to the second lens 144. For instance, as indicated in FIG. 5B, in the eye 200 where the distance from the cornea 210 to the fundus 230 is relatively long, the control unit 160 may obtain the distance D2' from the cornea 210 to the fundus 230 according to the second displacement X2' and move the first lens 142 on the light axis C. At this time, there is a displacement y' between the light axis C' of the image sensor 150 and the light axis C located at the pupil 220. In another aspect, as indicated in FIG. 5C, in the eye 200 where the distance from the cornea 210 to the fundus 230 is relatively short, the control unit 160 may obtain the distance D2" from the cornea 210 to the fundus 230 according to the second displacement X2" and move the first lens 142 on the light axis C. At this time, there is a displacement y" between the light axis C" of the image sensor 150 and the light axis C located at the pupil 220. In another embodiment of the invention, the control unit 160 may allow the first lens 142 and the light axis C to have a viewing angle therebetween, such that the image sensor 150 may focus on the fundus 230. Thereby, the control unit 160 may adjust the first lens 142 according to the distribution of the second light point images detected by the image sensor 150, such that the image sensor 150 may obtain the clear fundus images after focusing on the cornea 210.

In the present embodiment, the first lens 142 is disposed between the second lens 144 and the light sources 110, 120, and 130, and the second lens 144 is disposed between the first lens 142 and the image sensor 150, for instance. However, in another embodiment, the first lens 142 may be disposed between the second lens 144 and the image sensor 150, and the second lens 144 may be disposed between the first lens 142 and the light sources 110, 120, and 130. Other components, the material thereof, the arrangement thereof, each step in the auto-focusing method, the functions of said steps, and the effects achieved thereby are all similar to those described in the embodiment of the image capturing apparatus 100 shown in FIG. 1, and thus no further description is provided hereinafter.

To sum up, according to the descriptions of the image capturing apparatus and the auto-focusing method of the image capturing apparatus, the image capturing apparatus may focus on the cornea by detecting the first light point images that are obtained by transmitting the light beams to the cornea and may then focus on the fundus by detecting the second light point images on the fundus. Here, the second light point images are generated by substantially intersecting the light beams at the pupil and transmitting the light beams to the fundus. As a result, by applying the image capturing apparatus described herein, the time spent on focusing on the fundus may be reduced, and the clear fundus images may be obtained.

It will be apparent to those skilled in the art that various modifications and variations can be made to the structure of the disclosure without departing from the scope or spirit of the disclosure. In view of the foregoing, it is intended that the disclosure cover modifications and variations of this disclosure provided they fall within the scope of the following claims and their equivalents.

What is claimed is:

1. An auto-focusing method of an image capturing apparatus, the auto-focusing method comprising:
   transmitting a plurality of light beams from a plurality of light sources to an eye, wherein the eye comprises a cornea, a pupil, a crystalline lens, and a fundus, and the light beams are transmitted to the fundus through the cornea;
   detecting a plurality of first light point images on the cornea by an image sensor through a lens module, wherein the first light point images are generated by transmitting the light beams to the cornea, and the lens module comprises a first lens and a second lens;
   simultaneously moving the light sources and the first lens according to the first light point images and focal adjustment data, so as to focus on the cornea;
   detecting a plurality of second light point images on the fundus by the image sensor through the lens module, wherein the second light point images are generated by substantially intersecting the light beams at the pupil and transmitting the light beams to the fundus; and
   moving the first lens of the lens module according to the second light point images and the focal adjustment data, so as to focus on the fundus.

2. The auto-focusing method of the image capturing apparatus as recited in claim 1, wherein the step of moving the first lens of the lens module according to the first light point images and the focal adjustment data to focus on the cornea comprises:
   calculating a first set of location data of the first light point images;
   obtaining a first displacement corresponding to the first set of location data from the focal adjustment data according to the first set of location data; and
   adjusting the first lens and the light sources according to the first displacement.

3. The auto-focusing method of the image capturing apparatus as recited in claim 1, further comprising:
   detecting a cornea image of the cornea;
   obtaining a reflection difference of the cornea image according to distribution of the cornea image;
   adjusting the first lens according to the reflection difference and correction data; and obtaining the reflection difference every other time sequence according to the distribution of the cornea image.

4. The auto-focusing method of the image capturing apparatus as recited in claim 1, wherein the step of detecting the second light point images on the fundus by the image sensor through the lens module comprises:

obtaining a distance from the cornea to the fundus according to the second light point images and the focal adjustment data.

5. The auto-focusing method of the image capturing apparatus as recited in claim 1, wherein the step of detecting the second light point images on the fundus by the image sensor through the lens module further comprises:

calculating a second set of location data of the second light point images;

obtaining a second displacement corresponding to the second set of location data from the focal adjustment data according to the second set of location data; and adjusting the first lens according to the second displacement.

6. The auto-focusing method of the image capturing apparatus as recited in claim 1, further comprising:

detecting the first light point images by the image sensor through the first lens and detecting the second light point images by the image sensor through the first lens.

7. An image capturing apparatus comprising:

a plurality of light sources transmitting a plurality of light beams to an eye, wherein the eye comprises a cornea, a pupil, a crystalline lens, and a fundus, and the light beams are transmitted to the fundus through the cornea;

an image sensor;

a lens module disposed between the light sources and the image sensor, the lens module having a first lens and a second lens; and a control unit coupled to the image sensor and the lens module, wherein the image sensor detects a plurality of first light point images on the cornea through a lens module, the first light point images are generated by transmitting the light beams to the cornea, the control unit simultaneously moves the light sources and the first lens according to the first light point images and focal adjustment data, such that the image sensor focuses on the cornea, the image sensor detects a plurality of second light point images on the fundus through the lens module, the second light point images are generated by substantially intersecting the light beams at the pupil and transmitting the light beams to the fundus, and the control unit moves the first lens of the lens module according to the second light point images and the focal adjustment data, such that the image sensor focuses on the fundus.

8. The image capturing apparatus as recited in claim 7, wherein the control unit calculates a first set of location data of the first light point images, obtains a first displacement corresponding to the first set of location data from the focal adjustment data according to the first set of location data, and adjusts the first lens and the light sources according to the first displacement.

9. The image capturing apparatus as recited in claim 7, wherein the image sensor detects a cornea image of the cornea, and the control unit obtains a reflection difference of the cornea image according to distribution of the cornea image and adjusts the first lens according to the reflection difference and correction data.

10. The image capturing apparatus as recited in claim 9, further comprising:

a time sequence control unit coupled to the control unit, the time sequence control unit informing the control unit every other time sequence to obtain the reflection difference of the cornea image according to the distribution of the cornea image.

11. The image capturing apparatus as recited in claim 7, wherein the control unit obtains a distance from the cornea to the fundus according to the second light point images and the focal adjustment data.

12. The image capturing apparatus as recited in claim 7, wherein the control unit calculates a second set of location data of the second light point images, obtains a second displacement corresponding to the second set of location data from the focal adjustment data according to the second set of location data, and adjusts the first lens according to the second displacement.

13. The image capturing apparatus as recited in claim 7, wherein the image sensor detects the first light point images and the second light point images through the first lens.

* * * * *